US00PP08686P

United States Patent [19]

de Jong

[11] Patent Number: Plant 8,686

[45] Date of Patent: Apr. 12, 1994

[54] ALSTROEMERIA NAMED FLORENCE

[75] Inventor: Cornelis T. J. de Jong, Roelofarendsveen, Netherlands

[73] Assignee: AgroPlant-Select BV, De Kwakel, Netherlands

[21] Appl. No.: 36,651

[22] Filed: Mar. 24, 1993

[51] Int. Cl.[5] ..... A01H 5/00

[52] U.S. Cl. ..... Plt./87.1

[58] Field of Search ..... Plt. 87.1

*Primary Examiner*—James R. Feyrer

[57] ABSTRACT

A new and distinct cultivar of Alstroemeria plant named Florence, characterized by its predominanly dark pink flowers with outer petals having green tips and substantially dark pink color with some brown spotting occurring in highest concentration around the green tips; the two top inner petals are light pink at the base and dark pink at the apex and have a cream with yellow band and patterns of elongated brownish stripes; and, with the bottom inner petal being dark pink with elongated brownish stripes.

1 Drawing Sheet

BACKGROUND OF THE INVENTION

The present invention comprises a new and distinct cultivar of Alstroemeria plant referred to by the cultivar name Florence. Florence was originated from a hybridization program in Roelofarendsveen, The Netherlands in 1985. The female parent was an unnamed hybrid. The male parent was also an unnamed hybrid. Each of the parent plants were proprietary, and have not been released or marketed, and are maintained strictly for use in the breeding program. Florence was discovered and selected as one flowering plant within the progeny of the stated parentage by me on Jul. 21, 1985 in a controlled environment in Roelofarendsveen, The Netherlands. The first asexual reproduction of Florence was accomplished when vegative cuttings were taken from initial selection on Nov. 6, 1985 in a controlled environement in Roelofarendsveen in The Netherlands. Horticultural examination of selected units initiated in November 1985 has demonstrated that the combination of characteristics as herein disclosed in Florence are firmly fixed and retained through generations of asexual reproduction. The following observations, measurements and comparisons describe plants grown in Roelofarendsveen, The Netherlands under greenhouse conditions which approximate those generally used in commercial practice. The following traits have been repeatedly observed and are determined to be basic characteristics of Florence, which in combination distinguish this Alstroemeria from its parents and all other varieties of which I am aware:

1. The outer petals are distinctive dark pink with green tips and some mostly small brownish spots occurring in highest concentration around the green tips and around the vein pattern of the outer petals.

2. The inner portion of the body of the two top inner petals is light pink at the base, cream and yellow in the center, and the upper most portion of the body being dark pink similar to the color of the outer petals; the lowerr inner petal is dark pink and does not have a cream with yellow band.

3. Small brownish streaks appear on the inside portion of the inner petal body, increasing in length and width from the attachment point to the apex of each of these petals.

BRIEF DESCRIPTION OF THE FIGURE OF THE DRAWING

The accompanying photographic drawing of a close-up of the flower in bloom and buds shows typical inflorescence and foliage characteristics of Florence nearly as true as possible with illustrations of this type. In the following description, color references are made to the Royal Horticultural Society Colour Chart (RHS). The color values were determined in the afternoon in May 1988 under natural light conditions at Roelofarendsveen, The Netherlands.

BOTANICAL DESCRIPTION OF THE PLANT

Botanical: Alstroemeria cv Florence.
Commercial: Alstroemeria.

PLANT

A. General appearance:
- *Form.*—Typical of genus.
- *Height.*—Measured from the surface of the soil to the highest flowers: Summer: about 150–170 cm. Winter: about 170–225 cm. (If grown as a bedding plant outside, the average plant height will be about 50 cm during the summer and about 70 cm during the winter).
- *Growth.*—Fast, upright, spreading by rhizomes, bush forming.
- *Quality.*—Strong; thick stems, high flower production, less susceptible to high temperatures.

B. Foliage:
- *Quantity.*—Low-medium.
- *Number of leaves.*—Varying from season to season throughout the year.
- *Size of leaf.*—Length: Short to medium, about 7.5 cm. Width: Medium, about 2.75 cm.
- *Shape of leaf.*—Elliptical.
- *Color of leaf.*—Upper side: green. Under side: light green.

C. Rhizomes:
- *Color.*—White.
- *Size.*—Normal.

INFLORESCENCE

A. Bud:
- *Form.*—Normal.

*Size.*—Diameter: About 2.5 cm, just prior to opening. Length: About 3.75 cm.

*Receptacle.*—Broadly elliptical.

B. Flower:

*Size.*—Diameter: average about 6 cm.

*Borne.*—Umbel of about 5 branches of uniform length.

*Blooming habit.*—When grown under controlled conditions: continuous the year around (plant would bloom freely when grown as a bedding plant).

*Shape.*—Cupped.

*Outer petals.*—Shape: Lobed. Color: Body near to RHS 55-A with green tips and some pink and brownish spots occurring in highest concentration around the green tips and diminishing progrerssively along the vein patterns of the petals with increasing distance from the green tips. Reverse side: color near to RHS 55-A. Margins: very finely dentate.

*Inner petals.*—Shape: Lanceolate. Color: Upper inner petals: About slightly less than two-thirds of the inside portion of the body is cream and yellow colored near to RHS 2-B with the upper most portion near to RHS 55-A. Base has a hue of lighter pink. Small brownish sreaks appear on the inside portion of the inner petal body, increasing in length and width from the attachment point to the apex of each of these petals. Botton inner petal: Same color as the upper inner petals, about RHS 55-A, without the cream and yellow band; brown streaks are concentrated mostly around margins and apex. Reverse side: near to RHS 55-A with some brown spotting and near the margins brown streaking. Margins: crenate to smooth with few random projections.

*Peduncle.*—Color: Medium green. Length: About 12 cm.

*Fragrance.*—None.

*Lasting quality.*—Approximaely 14 days.

C. Reproductive organs:

*Stamens.*—Number 6.

*Anthers.*—Color: Olive green.

*Filaments.*—Color: Light purple.

*Pistils.*—Color: Anthocyanin. Number: 1.

*Stigma.*—Color: Anthocyanin with small spots.

*Fertility.*—High.

I claim:

1. A new and distinct cultivar of Alstroemeria plant named Florence, as described and illustrated, characterized by its predominantly dark pink flowers with outer petals having green tips and substantially dark pink color with some brown spotting occurring in highest concentration around the green tips; the two top inner petals are light pink at the base and dark pink at the apex and have a cream with yellow band and patterns of elongated brownish stripes; and, with the bottom inner petal being dark pink with elongated brownish stripes.

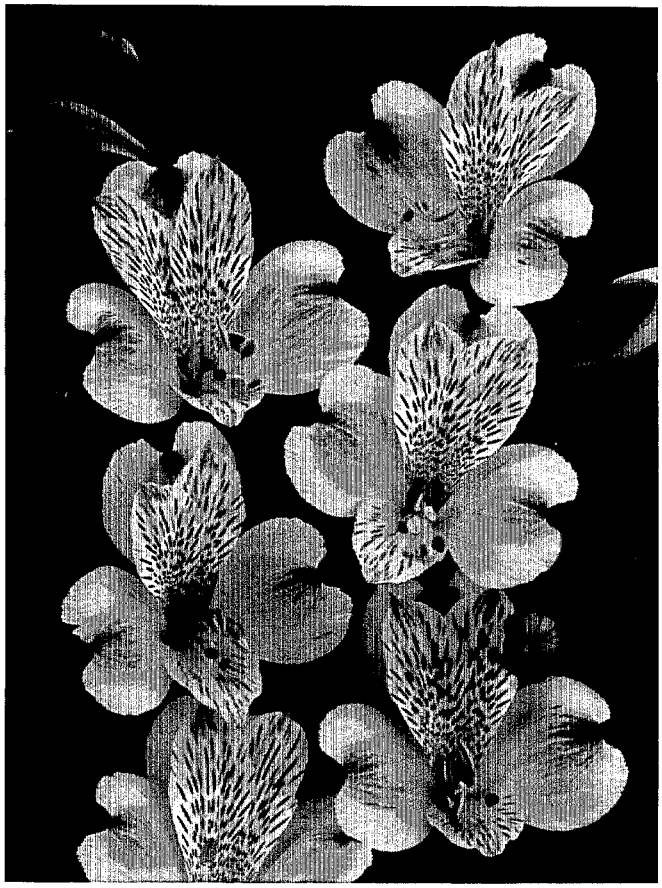

* * * * *